United States Patent
Shaw et al.

(10) Patent No.: US 8,950,238 B2
(45) Date of Patent: Feb. 10, 2015

(54) ODOR REMOVING DEVICE

(75) Inventors: Stephen H. Shaw, Vernon Hills, IL (US); Rachid M. Alameh, Crystal Lake, IL (US); William P. Alberth, Prairie Grove, IL (US); Jerome Vogedes, Milwaukee, WI (US)

(73) Assignee: Google Technology Holdings LLC, Mountain View, CA (US)

( * ) Notice: Subject to any disclaimer, the term of this patent is extended or adjusted under 35 U.S.C. 154(b) by 137 days.

(21) Appl. No.: 13/601,294

(22) Filed: Aug. 31, 2012

(65) Prior Publication Data

US 2014/0060150 A1 Mar. 6, 2014

(51) Int. Cl.
*G01N 7/00* (2006.01)

(52) U.S. Cl.
USPC ........................................................ 73/23.34

(58) Field of Classification Search
CPC .......... G01N 33/0001; G01N 33/0031; G01N 33/497; G01N 1/24; G06Q 10/10; G06Q 30/02; H04W 4/02; H04L 27/1225; H04L 29/7869; H04L 51/0072; H04L 51/0085; C08K 3/34; C12N 15/8286; C12N 15/8274; C12N 15/8245; C12N 15/8279; A01H 5/10; B65D 83/262; A61B 9/14; B05B 12/12; B05B 12/02; A61B 5/02042; A61M 1/3653; A61M 1/3656; A61M 2205/13
USPC ........................................................ 73/23.34
See application file for complete search history.

(56) References Cited

U.S. PATENT DOCUMENTS

| | | | |
|---|---|---|---|
| 6,372,951 B1 * | 4/2002 | Ter-Ovanesyan et al. | 604/361 |
| 6,422,061 B1 | 7/2002 | Sunshine et al. | |
| 7,035,647 B2 * | 4/2006 | de Verteuil | 455/456.1 |
| 7,673,820 B2 | 3/2010 | Ivri et al. | |
| 8,018,484 B2 | 9/2011 | Onodera | |
| 8,023,975 B2 * | 9/2011 | Wickman et al. | 455/466 |
| 8,038,577 B2 | 10/2011 | McIntosh | |
| 2003/0056569 A1 * | 3/2003 | Jansen | 73/23.34 |
| 2006/0256008 A1 * | 11/2006 | Rosenberg | 342/367 |

(Continued)

FOREIGN PATENT DOCUMENTS

| | | |
|---|---|---|
| JP | 2001336199 A | 12/2001 |
| WO | 2006059059 A1 | 6/2006 |

OTHER PUBLICATIONS

The Economic Times, "Now, a Mobile Phone That Can Smell", Apr. 24, 2012, 2 pages, http://articles.economictimes.indiatimes.com/2011-11-07/news/30369682_1_imec-moble-phone-monitoring.

(Continued)

*Primary Examiner* — Peter Macchiarolo
*Assistant Examiner* — Mohammed Keramet-Amircola
(74) *Attorney, Agent, or Firm* — Troutman Sanders LLP; James E. Schutz; Mark Lehi Jones

(57) ABSTRACT

A device is provided which includes an activity sensor, a communication portion, and a route suggesting portion. The activity sensor can detect physical activity of a user of a device. The communication portion may provide access one or more social networks via a communication network, in which the device may communicate with a social network of contacts. The route suggesting portion may provide an alternate route to travel such that the predicted odor may not offend others that are socially connected to the user and that travel the same routes as the user.

20 Claims, 10 Drawing Sheets

(56) References Cited

U.S. PATENT DOCUMENTS

| | | |
|---|---|---|
| 2010/0180667 A1* | 7/2010 | Bender et al. ............... 73/23.34 |
| 2010/0332668 A1* | 12/2010 | Shah et al. ................... 709/229 |
| 2011/0009986 A1* | 1/2011 | Page et al. ...................... 700/90 |
| 2012/0024042 A1* | 2/2012 | Vass et al. .................... 73/23.34 |
| 2012/0131985 A1* | 5/2012 | Brasfield ...................... 73/23.34 |
| 2012/0151993 A1* | 6/2012 | Brasfield ...................... 73/23.34 |
| 2013/0191458 A1* | 7/2013 | Krishnan et al. ............. 709/204 |
| 2014/0052369 A1* | 2/2014 | Han ............................... 701/428 |

OTHER PUBLICATIONS

Engadget, "Fujitsu Releases F-022 Fli9p Phone for Women Who Like to Smell Good", Apr. 24, 2012, 5 pages, http://www.engadget.com/2011/06/16/fujitsu-releases-f-022-flip-phone-for-women-who-like-to-smell-go/.

* cited by examiner

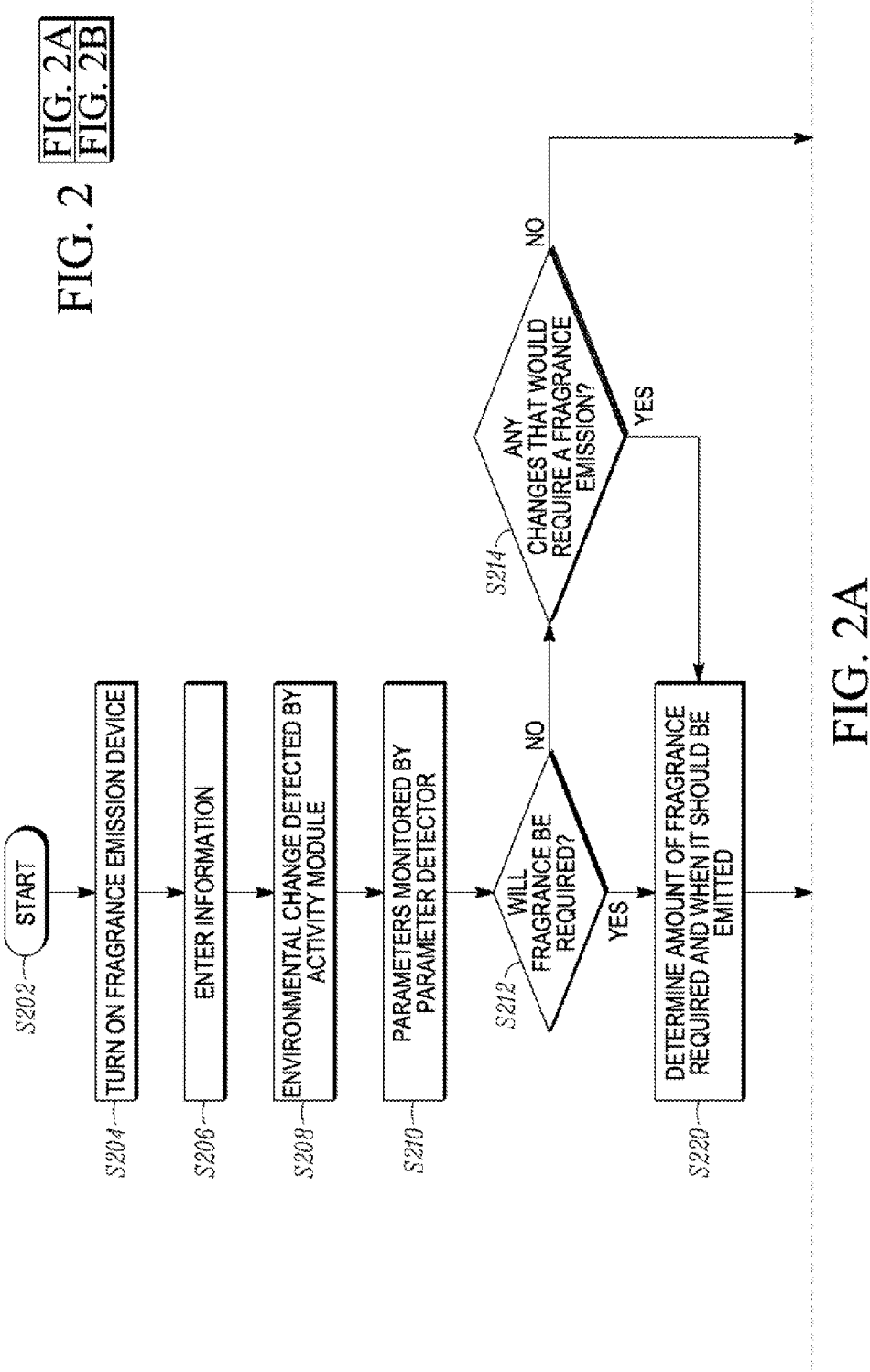

ODOR REMOVING DEVICE

CROSS REFERENCE TO RELATED APPLICATION

The present application is a continuation of co-pending and commonly assigned U.S. application Ser. No. 13/601,294, filed on 31 Aug. 2012, from which benefits under 35 USC 120 are hereby claimed and the contents of which are incorporated herein by reference.

TECHNICAL FIELD

Embodiments of the invention relate to a system for emitting a fragrance in response to detected parameters.

BACKGROUND

In some conventional automatic fragrance emission devices, fragrances are emitted in a slow and controlled manner (i.e., continuously emitting perfume throughout the day such that the fragrance does not wear off). In other automatic fragrance emission devices, a fragrance can be emitted automatically in response to physical characteristics such as body temperature. While conventional devices for emitting fragrances may be effective at fragrance emission, they do not include additional options for the user to customize and control the fragrance emission device.

BRIEF SUMMARY OF THE DRAWINGS

The accompanying drawings, which are incorporated in and form a part of the specification, illustrate example embodiments and, together with the description, serve to explain the principles of the invention. In the drawings.

DETAILED DESCRIPTION OF THE DRAWINGS

Figure 1:
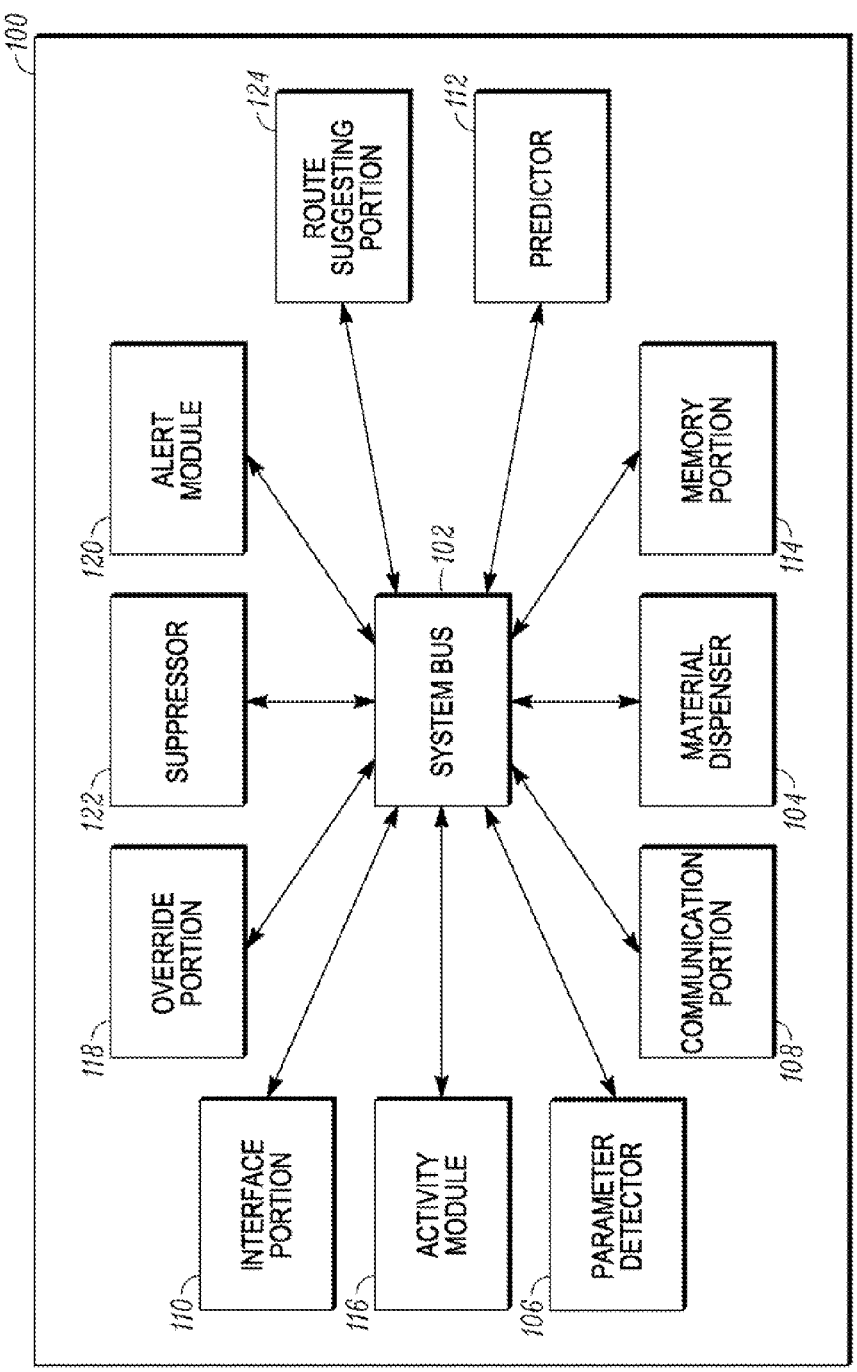
FIG. 1 illustrates a fragrance emission device in accordance with example embodiments.

As disclosed herein, an automatic fragrance emission device may include a system bus, a parameter detector, and a material dispenser. When the device is turned on, the parameter detector begins to monitor the surrounding environment for the parameter being detected. The parameter may be body temperature of the user, ambient temperature of the environment, speed of the user, heart rate, respiration rate, etc. Typically, there will be a threshold value for the desired parameter, and until the threshold value is reached, the parameter detector will not notify the alert module.

When the threshold value is reached, the parameter detector will notify the system bus that the threshold value has been reached, and the system bus will then signal the material dispenser to dispense the material within the device on to the user. The material may be dispensed for a pre-determined time before it stops.

Embodiments disclosed herein provide a fragrance emission device that can predict a need to emit fragrances in response to parameters, and then provide a user an opportunity to permit emission or override emission.

Embodiments disclosed herein provide a fragrance emission device that can predict a need to emit fragrances in response to parameters, including detection of other people surrounding the user and then provide a user an opportunity to permit emission, to override emission or alter his route to avoid the other people.

An example fragrance emission device described herein may be held or attached to the user's body or the user's clothing. However used, the device is able to detect changes that may signal a future need for a fragrance to be emitted by a material dispenser located within the device.

When a user is wearing the fragrance emission device and begins to exert himself or herself, an activity module within the device may detect the physical exertion. The activity module may detect a rise in sweat levels, an increase in body odor or body temperature, or any other parameter that may indicate the user is exercising or otherwise exerting themself.

When the activity module determines that the user is performing a physical activity, it alerts a predictor within the device. Non-limiting examples of a physical activity include a workout, working activities (e.g., construction work) or stress-induced activities (e.g., delivering an oral presentation). The predictor then uses the information provided by the activity module to predict when the user will generate body odor in the future, and when a fragrance will need to be applied to the user. For the purposes of brevity, the material applied to the user will be described as a fragrance, however, the material applied may also be an odor neutralizer, which would serve to neutralize or eliminate the body odor generated by the user instead of covering it up with a fragrance. In some embodiments, the predictor may also use information stored within the device regarding past instances where a fragrance was emitted, combine that information with the current information supplied by the activity module, determine when body odor will be generated by the user, and dispense an appropriate amount of fragrance at an appropriate time.

Once the predictor determines when the user will begin to generate body odor, an optional alert module located within the device may alert the user of the situation and let the user know when the fragrance will be emitted. The user will then have the opportunity to override the impending fragrance emission, based on the current circumstances of the user. For instance, the user may be planning on showering immediately after the physical activity, and therefore may choose to reject the fragrance emission. Should the user choose to reject the fragrance emission, a suppressor located within the device will cancel the scheduled fragrance emission such that the material dispenser will not dispense the fragrance at the scheduled time. Should the user choose to accept the fragrance emission instead, the suppressor will not cancel the scheduled fragrance emission, and the material dispenser will dispense the fragrance at the scheduled time.

In addition to the features listed above, embodiments may include the ability to connect to a network (e.g., satellite, Wi-Fi, cellular, etc.) to track locations of the user's contacts via social networking sites or other location tracking services. In some cases, the device may learn that some of the user's social contacts (i.e., persons previously known to the user) are in the same area as the user and therefore may possibly meet the user within the area or on a similar route that the user is likely to take. However, to avoid subjecting the social contacts to the odor, the device may include a route suggesting portion that can notify the user that his contacts are in the area. The route suggesting portion may additionally provide an alternate route for the user to take to increase the chances of avoiding an unpleasant odorous meeting with his social contacts. The route suggesting portion may employ searching technology such as Google Maps® or Google Earth® to supply the alternate route.

The aspects of embodiments will now be further described with reference to FIGS. 1-3C.

FIG. 1 illustrates a fragrance emission device 102 in accordance with example embodiments.

As shown in the figure, fragrance emission device 102 includes a system bus 102, a material dispenser 104, a parameter detector 106, a communication portion 108, an interface portion 110, a predictor 112, a memory portion 114, an activity module 116, an override portion 118, an alert module 120, a suppressor 122 and a route suggesting portion 124.

System bus 102 is arranged to bi-directionally communicate with each of material dispenser 104, parameter detector 106, activity module 116, communication portion 108, interface portion 110, predictor 112, memory portion 114, override portion 118, alert module 120, suppressor 122 and route suggesting portion 124.

In this example, each of material dispenser 104, parameter detector 106, activity module 116, communication portion 108, interface portion 110, predictor 112, memory portion 114, override portion 118, alert module 120, suppressor 122 and route suggesting portion 124 communicate with each other via system bus 102. However, in other embodiments, each of material dispenser 104, parameter detector 106, activity module 116, communication portion 108, interface portion 110, predictor 112, memory portion 114, override portion 118, alert module 120, suppressor 122 and route suggesting portion 124 may be configured to communicate directly with each other without the need for system bus 102.

In this example, system bus 102, material dispenser 104, parameter detector 106, activity module 116, communication portion 108, interface portion 110, predictor 112, memory portion 114, override portion 118, alert module 120, suppressor 122 and route suggesting portion 124 are distinct devices. However, in other embodiments, at least two of system bus 102, material dispenser 104, parameter detector 106, activity module 116, communication portion 108, interface portion 110, predictor 112, memory portion 114, override portion 118, alert module 120, suppressor 122 and route suggesting portion 124 may be combined as a unitary device. Further, in some embodiments, at least one of system bus 102, material dispenser 104, parameter detector 106, activity module 116, communication portion 108, interface portion 110, predictor 112, memory portion 114, override portion 118, alert module 120, suppressor 122 and route suggesting portion 124 may be implemented as non-transient, tangible computer-readable media for carrying or having computer-executable instructions or data structures stored thereon. Such non-transient, tangible computer-readable media can be any available media that can be accessed by a general purpose or special purpose computer. Non-limiting examples of non-transient, tangible computer-readable media include physical storage and/or memory media such as RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications connection (hardwired and/or wireless, or a combination of hardwired or wireless) to a computer, the computer properly views the connection as a non-transient, tangible computer-readable media computer-medium. Thus, any such connection is properly termed a non-transient, tangible computer-readable medium. Combinations of the above should also be included within the scope of non-transient, tangible computer-readable media.

System bus 102 is operable to bidirectionally communicate with material dispenser 104, parameter detector 106, activity module 116, communication portion 108, interface portion 110, predictor 112, memory portion 114, override portion 118, alert module 120, suppressor 122 and route suggesting portion 124 and is configured to coordinate between all of the portions within fragrance emission device 102 to control the fragrance output desired by the user. In some embodiments at least two of material dispenser 104, parameter detector 106, activity module 116, communication portion 108, interface portion 110, predictor 112, memory portion 114, override portion 118, alert module 120, suppressor 122 and route suggesting portion 124 may be arranged to communicate directly with one another without coordination from system bus 102. An example embodiment of system bus 102 will be further described with reference to FIG. 2 (represented by FIGS. 2A and 2B).

Material dispenser 104 is operable to bidirectionally communicate with system bus 102. Non-limiting examples of material dispenser 104 include a fan to dispense the material, a sprayer to spray the material, thermal system to vaporize the material, or other system to urge material out of fragrance emission device 102 to the desired area.

Material dispenser 104 may receive a signal from system bus 102 to dispense fragrant material. Material dispenser 104 may then dispense the fragrant material. In some embodiments, material dispenser 104 may dispense the material for a predetermined period. In some embodiments, material dispenser 104 may continue to dispense the material until further instructed by system bus 102. In some embodiments, material dispenser 104 may additionally send a signal to system bus 102 indicating when the supply of fragrant material is low or needs to be replaced.

Parameter detector 106 is operable to bidirectionally communicate with system bus 102. Parameter detector 106 may be configured to detect parameters such as heat, moisture, odor, speed, or any other parameter that may be detected by conventional detectors or sensors such as motion sensors (such as accelerometers), biometric sensors (such as galvanic skin response monitors), visual sensors (such as cameras), temperature sensors (such as thermocouples) or odor sensors (such as electronic noses). Parameter detector 106 may be configured to detect an amount of a parameter, a change in a parameter or combinations thereof. For example, parameter detector 106 may include an odor sensor configured to detect a change in odor intensity.

In some embodiments, parameter detector 106 monitor parameters and to relay such information back to system bus 102. For example, parameter detector may send a notification to system bus 102 when a specific parameter reaches a threshold value, e.g., when the user's odor level reaches a predetermined point.

Communication portion 108 is operable to bidirectionally communicate with system bus 102, and is operable to send and receive signals from communication networks external to the housing of the device. Non-limiting examples of external communication networks include satellite communication networks, cellular communication networks and wired or wireless Internet communication networks.

Communication portion 108 may access various social networks, personal calendars or other such systems via the communication networks in order to provide data to system bus 102 for use in determining fragrance emission schedules and patterns. Social networks may include a social structure that is connectable over a communication network, i.e., the Internet, a wireless or wired communication network, wherein the social structure includes a set of actors (such as individuals or organizations) and the dyadic ties between these actors. Examples of social networks include websites that allow individuals to compile a list of friends, contacts or business associates and communicate with those contacts via the Internet. Non-limiting examples of social networks include Google+®, Facebook®, Twitter® and LinkedIn®.

Interface portion 110 is operable to bidirectionally communicate with system bus 102. Interface portion 110 may include a graphical user interface, or any other interface into which data may be input by a user and from which data may be displayed to a user.

In operation, interface portion 110 enables the user to input data to fragrance emission device 102 via system bus 102 regarding various preferences and data regarding preferred fragrance emissions. Interface portion 110 may provide alerts or prompts regarding impending fragrance emissions. Interface portion 110 will be further described with reference to FIG. 3.

Predictor 112 is operable to bidirectionally communicate with system bus 102. Predictor 112 may include a processor that is operable to predict an odor to be present at a future time based on information provided to system bus 102 from parameter detector 106 and activity module 116. The processor may additionally be operable to output a prediction signal based on the prediction. In essence, predictor 112 may determine when a fragrance emission will be required, and how much fragrance may be required.

In operation, predictor 112 receives information from parameter detector 106, via system bus 102, regarding parameters that have been sensed. In some embodiments, predictor 112 may then communicate with memory portion 114, via system bus 102, to compare data of currently detected parameters with stored data to determine an appropriate response. Once an appropriate response has been determined, predictor 112 relays that response, via system bus 102, interface portion 110, alert module 120 and material dispenser 104.

Predictor 112 may rely on a priori data to make its predictions of a future time as to when a fragrance should be emitted. The data may include previous data stored in memory portion 114 from previous fragrance emission instances, but it may also include data stored in memory portion 114 by the user via interface portion 110. Non-limiting examples of such data include the sweat history of the user, the odor history of the user, the typical exercise schedule of the user, the rate at which the user exercises, the user's calendar containing meetings and appointments, the ambient temperature in which the user typically exercises, etc. The above data examples are intended to be non-limiting examples of the types of data upon which predictor 112 may rely in order to make its predictions, and any other types of data that may be relevant to making an accurate prediction may also be used. Predictor 112 may rely on a single piece of data to make its prediction, but it may also rely on a combination of many different data to make its prediction. For instance, there may be a relationship between multiple parameters that may help determine the appropriate time to dispense a fragrance and the appropriate amount of fragrance to dispense. For example, predictor 112 may be able to accurately predict when the user will need to be sprayed with a fragrance, and how much fragrance to spray, based on a combination of the user's sweat history, odor history and ambient temperature in which the user is exercising. Predictor 112 may use any known functional relational system or method, non-limiting examples of which include a functional algorithm or lookup table.

Memory portion 114 is operable to bidirectionally communicate with system bus 102. Memory portion 114 may include a tape drive, magnetic disk, optical disk, flash memory, ROM memory, RAM memory, DRAM memory, SRAM memory, or any other manner by which data may be stored in a small space.

Memory portion 114 is arranged to receive, via system bus 102, information regarding parameter detection from parameter detector 106 and fragrance emission patterns from material dispenser 104. Memory portion 114 may then store the information for future reference by system bus 102 when determining a fragrance emission plan based on current conditions.

Activity module 116 is operable to bidirectionally communicate with system bus 102. Activity module 116 may include any devices capable of detecting changes in physical activity level of a user. As changes in physical activity are typically accompanied by an increase in speed or movement of the person undertaking the physical activity, an example embodiment of activity module 116 may be an accelerometer.

In some embodiments, activity module 116 may receive a signal from system bus 102 to begin monitoring an activity or for changes in activity level. Activity module 116 receives information from the user regarding the physical activity of the user. Activity module may notify system bus 102 when an activity, or a change in activity, has occurred, and system bus 102 may then signal parameter detector 106 to actively monitor various other parameters that may determine if fragrance emission at a future time is required.

In some embodiments, parameter detector 106 and activity module 116, combined, may be considered an activity sensor that is able to detect physical activity of the user.

Override portion 118 is operable to bidirectionally communicate with system bus 102. Override portion 118 generates an override signal, via interface portion 110 and system bus 102, when an impending fragrance emission is undesirable by the user. Override portion 118 provides, via system bus 102, the override signal to suppressor 122.

Alert module 120 is operable to bidirectionally communicate with system bus 102. Alert module 120 alerts the user of a fragrance emission in a future time by communicating with interface portion 110 (either indirectly via system bus 102 or via direct communication between alert module 120 and interface portion 110) and prompting the user to accept or reject the upcoming fragrance emission. In some embodiments, alert module 120 may alert the user of an impending odor. Additionally, alert module 120 may alert the user that an alternate route is required, as determined by route suggesting portion 124, due to the proximity of the user to other persons in the area. In some example embodiments, alert module 120 and route suggesting portion 124 are a unitary portion. In some example embodiments, alert module 120 and route suggesting portion 124 are separate portions. Types of alerts may include audio (such as a loud beeping noise), visual (such as a flashing light or textual notification) and/or mechanical (such as a vibration).

Suppressor 122 is operable to bidirectionally communicate with system bus 102. Upon receiving an override signal, suppressor 122 provides a suppression signal, via system bus 102, to material dispenser 104 thus preventing dispensing of material as originally scheduled.

Route suggesting portion 124 is operable to bidirectionally communicate with system bus 102. Route suggesting portion 124 receives notification from system bus 102 (via indirection communication with communication portion 108) or from communication portion 108 (via direct communication) that it may be likely that the user will encounter some of her social contacts while exercising. Route suggesting portion then determines an alternate route that the user may take to avoid the social contacts, and sends the information to the user. The determination of an alternate route may be based on knowledge of previous routes traveled by the user that may be stored in memory portion 114, or they may be generated via services such as Google Maps® or MapQuest® that route suggesting portion 124 may access via communication portion 108.

Figure 2B:
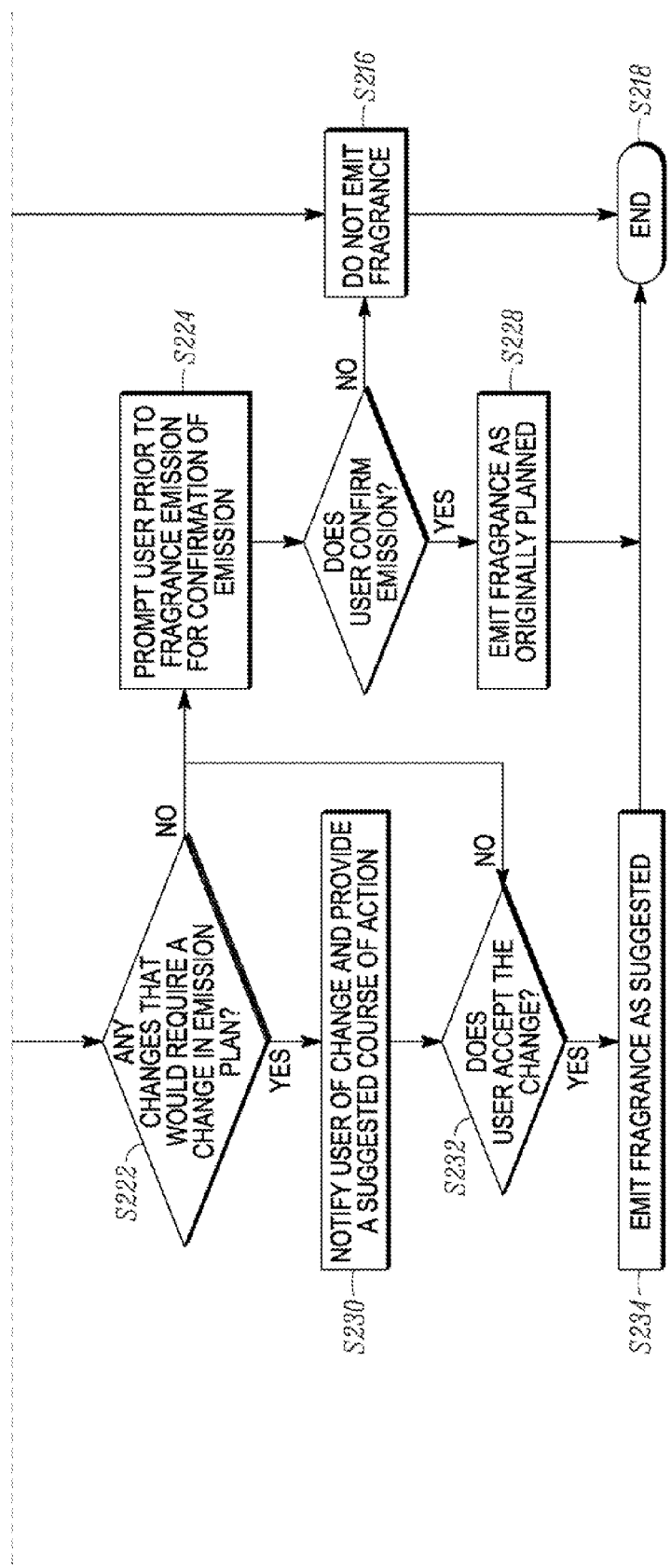
FIG. 2, represented by FIGS. 2A and 2B, illustrates a method of emitting a fragrance in accordance with example embodiments.

FIG. 2, (represented by FIGS. 2A and 2B), illustrates an example method 200 by which fragrance emission device 102 emits a fragrance.

In the following discussion regarding FIG. 2, there may be reference to one or more of system bus 102, material dispenser 104, parameter detector 106, activity module 116, communication portion 108, interface portion 110, predictor 112, memory portion 114, override portion 118, alert module 120, suppressor 122 or route suggesting portion 124 communicating with each other. The communications between the above referenced components may be direct communications between the components or indirect communications that are fed through system bus 102.

Once fragrance emission device 102 is enabled, information is added (S206). For example, returning to FIG. 1, interface portion 110 may prompt the user to provide information. In an example embodiment, the information provided by the user may include medical history, access to personal or business calendars, access to social networking sites, typical schedules of physical activities, fragrance preferences (i.e., how strongly the user or others in social network typically likes fragrances applied), and any other information that may be useful for fragrance emission device 102 to have in order to appropriately predict the need for fragrance emission. In some embodiments, entering information may occur the first time device 102 is activated. In some embodiments, entering information may also occur whenever new information is available to the user that would be beneficial for predicting fragrance emission needs. In some embodiments, once all information has been input, system bus 102 provides information regarding communications (passwords for calendars, social networking sites, etc.) to communication portion 108, which uses that information to connect to the user's accounts. Other static information, such as medical history, other user preferences, or past fragrance emission data, may then be stored in memory portion 114 to be accessed at a later time.

Returning to FIG. 2, after the user has entered information, the environment is monitored (S208). For example, returning to FIG. 1, system bus 102 sends a signal instructing activity module 116 to begin monitoring the user and/or the environment for changes that may require a future fragrance emission. For purposes of explanation, the change being monitored in this example is change in locomotion speed, wherein the user is taking a brisk walk outside on a lunch break.

Parameters are then detected (S210). For example, returning to FIG. 1, activity module 116 senses the change in walking speed and notifies system bus 102 and parameter detector 106 of the change. Parameter detector 106 then begins to actively monitor the desired parameter. It can be appreciated by one of ordinary skill in the art that any number of parameters may be monitored to provide the desired outcome (i.e., odor generation, sweat generation, body temperature, etc.). However, for purposes of explanation, the parameter being detected in this example is the amount of odor generated by the user. If the amount of odor generated by the user reaches a threshold level, parameter detector 106 will notify system bus 102. The threshold level may be determined by a number of factors, including medical history, odor generation history of the user that is stored in memory portion 114, or specific preferences entered by the user via interface portion 110.

Returning to FIG. 2, it is then determined whether a fragrance will be required (S212). For example, returning to FIG. 1, fragrance emission device 102 may then determine whether a fragrance emission will be required (S212). As discussed above in the example embodiment, until a threshold level of odor is generated, no fragrance will be required. If the user takes a short walk and does not generate enough odor to reach the threshold, fragrance will not be emitted. However, there may be other circumstances in which the user would desire a fragrance to be emitted even without reaching the odor generation threshold. For instance, communication portion 108 may learn that some social contacts of the user are located along the path on which the user is walking, and system bus 102 would be notified. Route suggesting portion 124 would generate an alternate route for the user such that the user's contacts could be avoided. Alert module 120 would then alert the user via interface portion 110 of the impending meeting with social contacts and provide a choice of taking the alternate route suggested by route suggesting portion 124 or emitting a fragrance to improve the user's odor even though the odor generation threshold was not reached.

Returning to FIG. 2, if the user decides to take the alternate route suggested by route suggesting portion 124, the change relayed to the user by fragrance emitting device 102 does not require a change in the fragrance emission plan (No at S214), the fragrance is not emitted (S216), and method 200 ends (S218). If a fragrance is required, the amount and time of emission is then determined (S220). For example, returning to FIG. 1, if the user generates enough odor during the walk to reach the threshold level for odor generation, parameter detector 106 sends a signal to system bus 102 as notification that the threshold level has been reached. The signal also serves as notification that fragrance emission will be required. Next, fragrance emission device 102 must determine the amount of fragrance required and when it should be emitted (S220).

In an example embodiment, returning to FIG. 1, in order to make the determination, information regarding the amount of odor generated is forwarded from system bus 102 to predictor 112. Predictor 112 then compares the current conditions to past instances in which the user required fragrance emission based on the level of odor being generated during physical activity. The current conditions will include the level of odor being generated, but it may also include other conditions that may be sensed by parameter detector 106, non-limiting examples of such conditions include the outside temperature, the rate of activity, the length of time the user has been walking, and any other parameter that may help to predict when a fragrance would need to be emitted based on the odor level being generated by the user.

As a non-limiting example, predictor 112 may find a past instance within memory portion 114 in which the user was walking at a similar pace, but the outside temperature was lower than the current conditions. Stored user feedback from this instance may have instructed fragrance emission device 102 that the amount of fragrance emitted was not sufficient. In addition, predictor 112 may find a different past instance within memory portion 114 in which the user was walking at a different pace, but the outside temperature was the same as the current conditions, and user feedback from this instance may have indicated that the amount of fragrance emitted was the correct amount. Using such information, predictor 112 will determine the appropriate time at which to emit the fragrance, and how much fragrance to emit to appropriately counteract the odor being generated by the user.

It is then determined whether there is a change in the planned emission (S222). For example, fragrance emission device 102 continues to monitor the user and environmental conditions to continue revising the fragrance emission plan as required, and also to determine whether or not any changes by the user, environmental conditions or social conditions would require a change in the fragrance emission plan.

If there are no changes that would require a change in the fragrance emission plan (No at S222), the user receives a notification or prompt prior to when the fragrance is emitted in order to confirm the user's desire for the fragrance to be emitted (S224). For example, returning to FIG. 1, predictor 112 provides alert module 120 with the fragrance emission plan. Alert module 120 then provides interface portion 110 with information regarding the upcoming fragrance emission. Interface portion 110 then relays the information to the user and provides a sensory alert and/or a sound or vibration to notify the user that an action is required.

It is then determined whether the emission is confirmed (S226). For example, the user may confirm the fragrance emission as planned, or may override the planned emission. In one instance, the user may be planning on taking the rest of the day off after the walk, after which the user will go home and shower.

If the user does not believe the fragrance emission is required, the user may override the planned emission (No at S226). For example, returning to FIG. 1, the user inputs the decision to override the upcoming fragrance emission via interface portion 110, which relays the information to override portion 118. Suppressor 122 then suppresses the signal that would have triggered material dispenser 104 to dispense the fragrance. Returning to FIG. 2, in such a case, the fragrance is not emitted (S216) and method 200 ends (S218).

Now consider the case where the user may confirm the planned emission (Yes at S226). For example, the user may be planning on going back to work after the walk, and thus believes that the fragrance emission is still required. Returning to FIG. 1, the user inputs the decision to accept the upcoming fragrance emission via interface portion 110, which relays the information to alert module 120. Alert module 120 then relays the signal to material dispenser 104 to emit the fragrance as planned.

Returning to FIG. 2, if the fragrance emission plan is confirmed (Yes at S226), the fragrance is emitted as planned (S228) and method 200 ends (S218).

Now consider the situation where there is a change in the emission plan (Yes at S222). For example, in an alternative scenario, while the user is briskly walking a request for an urgent business meeting is sent to the user's email. The urgent business meeting may be scheduled to start within the next 30 minutes, whereas the user had not originally planned on seeing anyone or meeting with anyone for the next 60 minutes. The change in timing would require a change in the fragrance emission plan.

In an example embodiment, returning to FIG. 1, communication portion 108 receives the meeting request and provides the updated calendar information to system bus 102, which forwards the data to memory portion 114 and predictor 112. Using data from memory portion 114 and the updated calendar information, predictor 112 updates the fragrance emission plan and forwards the new plan to alert module 120. Alert module 120 forwards the information to interface portion 110 to notify the user.

If there is a change in the emission plan, the user is notified (S230). For example, the user is then notified that an urgent meeting has been called and the fragrance emission plan has changed based on the updated calendar information.

It is then determined whether the change is accepted (S232). For example, the user decides whether or not to accept the change. In one instance, the user may decide that the meeting is not very important and decline the meeting invitation (No at S232). In an example embodiment, returning to FIG. 1, the user enters the decision to decline the meeting invitation into interface portion 110. The decision is then sent to system bus 102, which forwards the information to communication portion 108. Communication portion 108 then responds to the message to decline the meeting request.

The user then receives a notification or prompt prior to when the fragrance is emitted in order to confirm the user's desire for the fragrance to be emitted, and the method continues as discussed above (return to S224).

Now consider the situation where the user accepts the suggested course of action (Yes at S232). For example, the user may instead choose to accept the meeting and thus accept the change in the fragrance emission plan. In an example embodiment, returning to FIG. 1, the user enters the decision to accept the meeting invitation into interface portion 110. The decision is then sent to system bus 102, which forwards the information to communication portion 108. Communication portion 108 then responds to the message to accept the meeting request. Alert module 120 is also notified of the user's acceptance of the modified fragrance emission plan, and provides a signal to material dispenser 104 to emit the fragrance per the modified plan at the appropriate time.

Returning to FIG. 2, the fragrance is emitted as suggested (S234) and method 200 ends (S218).

Figure 3A:
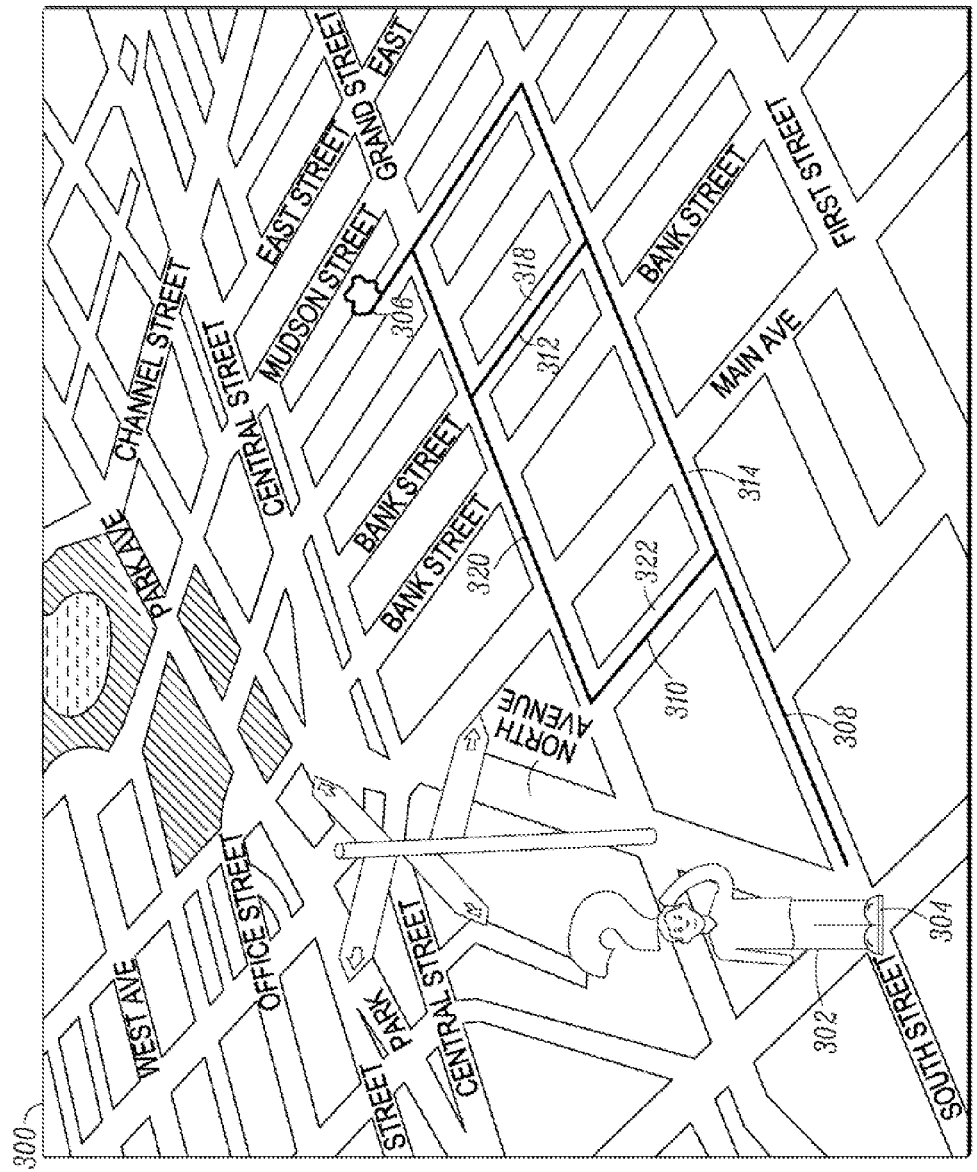
FIGS. 3A-C illustrate an example embodiment of a fragrance emission device suggesting an alternative travel route
Figure 3B:
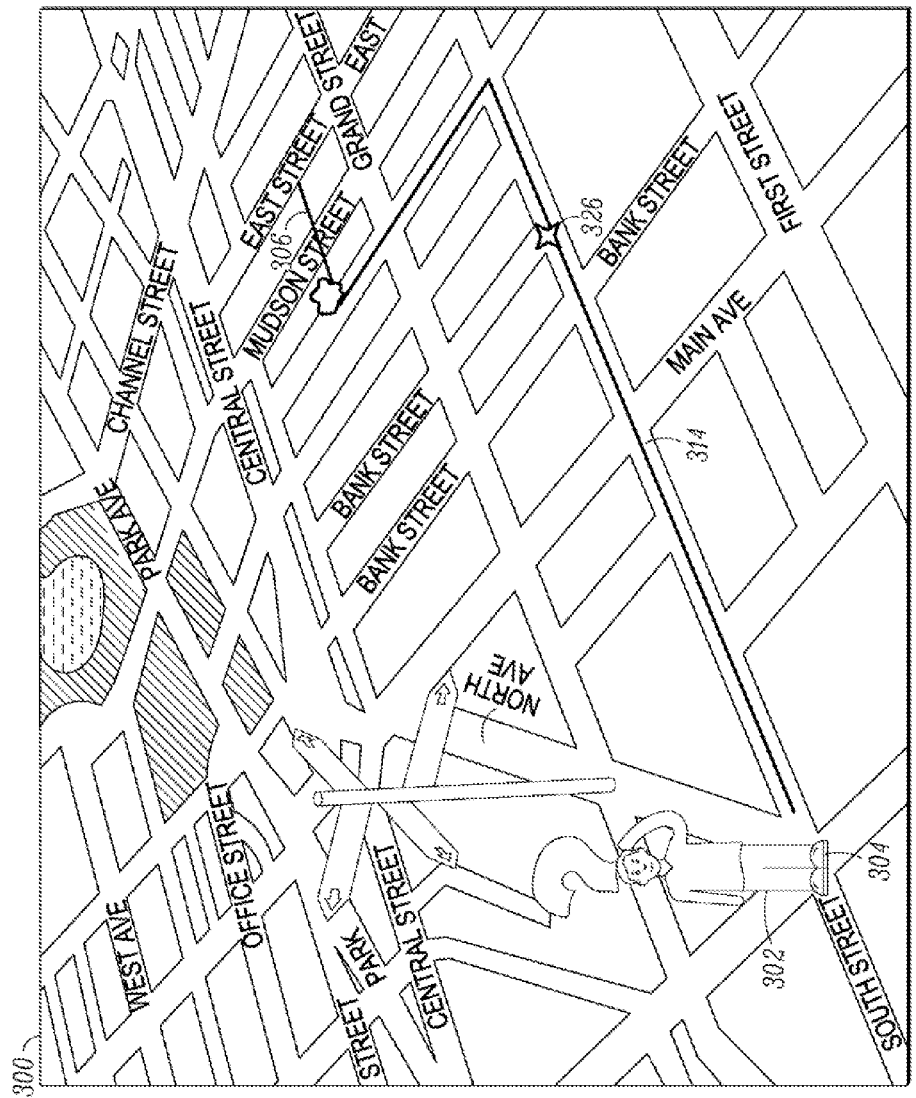
Figure 3C:
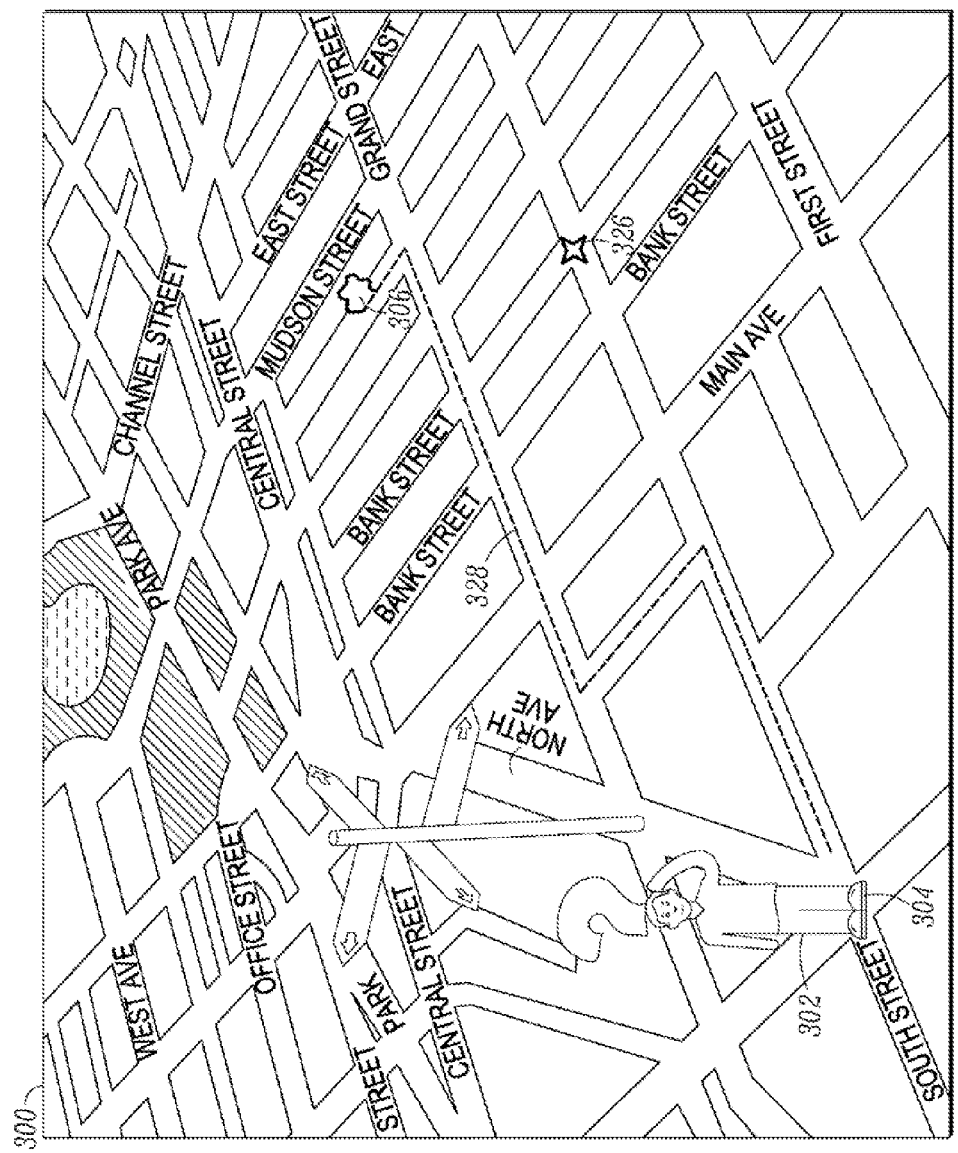

FIGS. 3A-3C illustrate an example embodiment of a fragrance emission device suggesting an alternative travel route.

FIG. 3A shows a screen shot of a graphic user interface of an embodiment of a fragrance emission device 102, which includes a navigating application. In the figure, a map 300 shows a plurality of streets, an icon 302 of the user at position 304 and an icon 306 of the user's destination. This screen shot additionally includes a first travel route 308, a second travel route 310 and a third travel route 312, with which the user may from position 304 to destination 306. These travel routes may be provided by any known system or method included a GPS system, a Wi-Fi system or a memory which as stored the travel routes as previously traveled.

For purposes of discussion, presume that the user of fragrance emission device 102 has just finished strenuously exercising, to the point where fragrance emission device 102 is predicting that the user will have a bad odor. Further presume that fragrance emission device 102 is aware that user, at position 304, is walking to destination 306. This awareness may be provided by any known method, non-limiting examples of which include the user providing the information via the user interface. As shown in FIG. 3B, still further presume that first travel route 308 is the quickest route to destination 306, so the user is intending to travel along first travel route 308, as shown by line 324. As shown in FIG. 3B, additionally presume that one of the user's social contacts is located at position 326, along first travel route 308.

In accordance with this embodiment, fragrance emission device 102 is able to notify the user by providing an icon at position 326 to warn the user that there is a likelihood of contacting the social contact while traveling along first travel route 308.

Fragrance emission device 102 would then notify the user that the work or social contacts were approaching, and an alternative route may be provided to the user. The alternative route may be generated as discussed with reference to route suggesting portion 124 and provided to the user. For example, as shown in FIG. 3C, an alternate route 328 is shown as dotted line on the user interface. Here, alternate route 328 corresponds to second travel route 310 (as shown in FIG. 3A). If the user were to take the suggested alternate route, he may avoid his social contact at position 326, thus avoid subjecting the social contact to the bad odor.

In an alternative embodiment, in which the user is in an untraveled area, an alternative route may be generated by route suggesting portion 124 after route suggesting portion 124 chose an appropriate route from any known navigation provider, such as Google Maps® or MapQuest®.

One skilled in the art would appreciate that the scenario described above is but one non-limiting example scenario in which fragrance emission device 102 may be used. Fragrance emission device 102 may also be configured to detect changes in lighting or music that may indicate the user is having a romantic dinner, in which case a fragrance may be emitted. Fragrance emission device 102 may also be configured to detect an impending chance encounter with a social contact, in which case a fragrance may be emitted. In another embodiment, fragrance emission device 102 may be configured to provide a suggested route based on a historical traffic pattern, for example as stored in memory portion 114, for which fragrance emission device 102 has previously traveled. In another embodiment, fragrance emission device 102 may be configured to provide a suggested route based on the ventilation present, for example as stored in memory portion 114, along the routes for which fragrance emission device 102 has previously traveled. For example, route suggesting portion 124 may determine two potential alternative routes for the user, and memory portion 114 may have stored data regarding the air quality or ventilation for the two routes (e.g., the user has previously traversed those routes and provided such air quality or ventilation information). The resulting route suggested to the user may be based on the user's preferences regarding air quality. It can be appreciated that there are many scenarios in which fragrance emission device 102 may be useful in detecting parameters and predicting when an emission of fragrance will be required.

Additionally, it can be appreciated that the more the device is used the more information will be stored in memory portion 114, and predictor 112 will be able to provide more accurate fragrance emission predictions for the user.

Example working embodiments of fragrance emission mechanisms of fragrance emission devices will now be described with reference to FIGS. 4-7.

Figure 4:
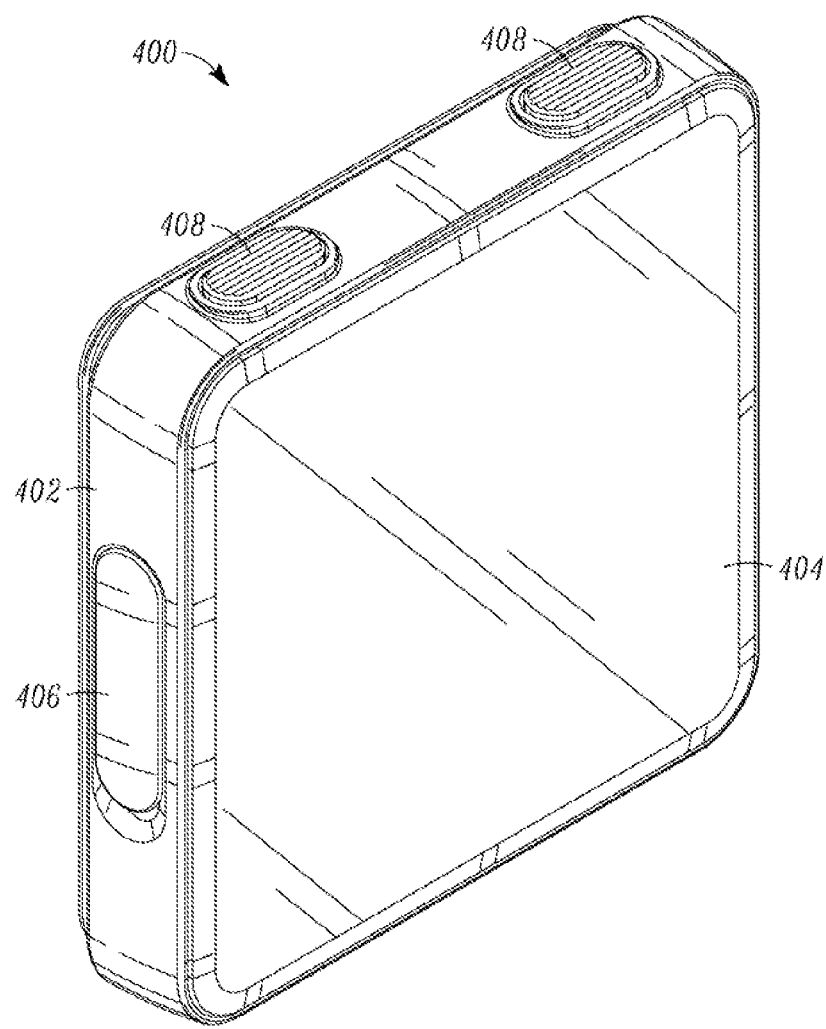
FIG. 4 illustrates an oblique view of a front side of an example fragrance emission device.

FIG. 4 illustrates an oblique view of a front side of an example fragrance emission device 400. As shown in the figure, fragrance emission device 400 includes a body 402, a display screen 404, a power button 406 and air intake vents 408.

Figure 5:
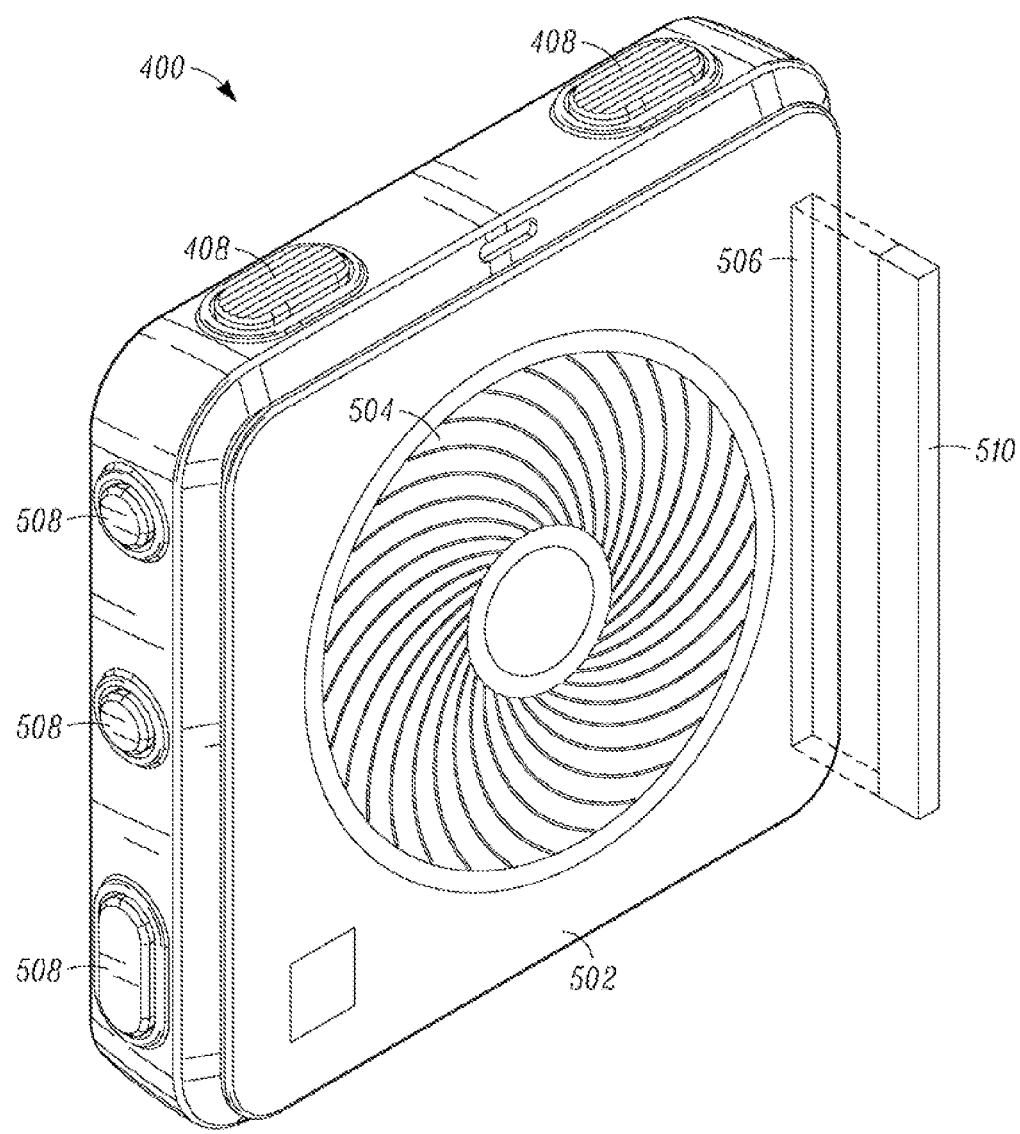
FIG. 5 illustrates an oblique view of a back side of the fragrance emission device of FIG. 4.

FIG. 5 illustrates an oblique view of a back side 502 of fragrance emission device 400. As shown in the figure, fragrance emission device 400 additionally includes an exhaust vent 504, a fragrant material loading port 506 and a plurality of actuating buttons 508. Additionally shown in the figure, a fragrant material 510 may be loaded into body 402 via fragrant material loading port 506. The fragrant material may be composed of a solid or gel-like material and is replaceable upon degradation.

Figure 6:
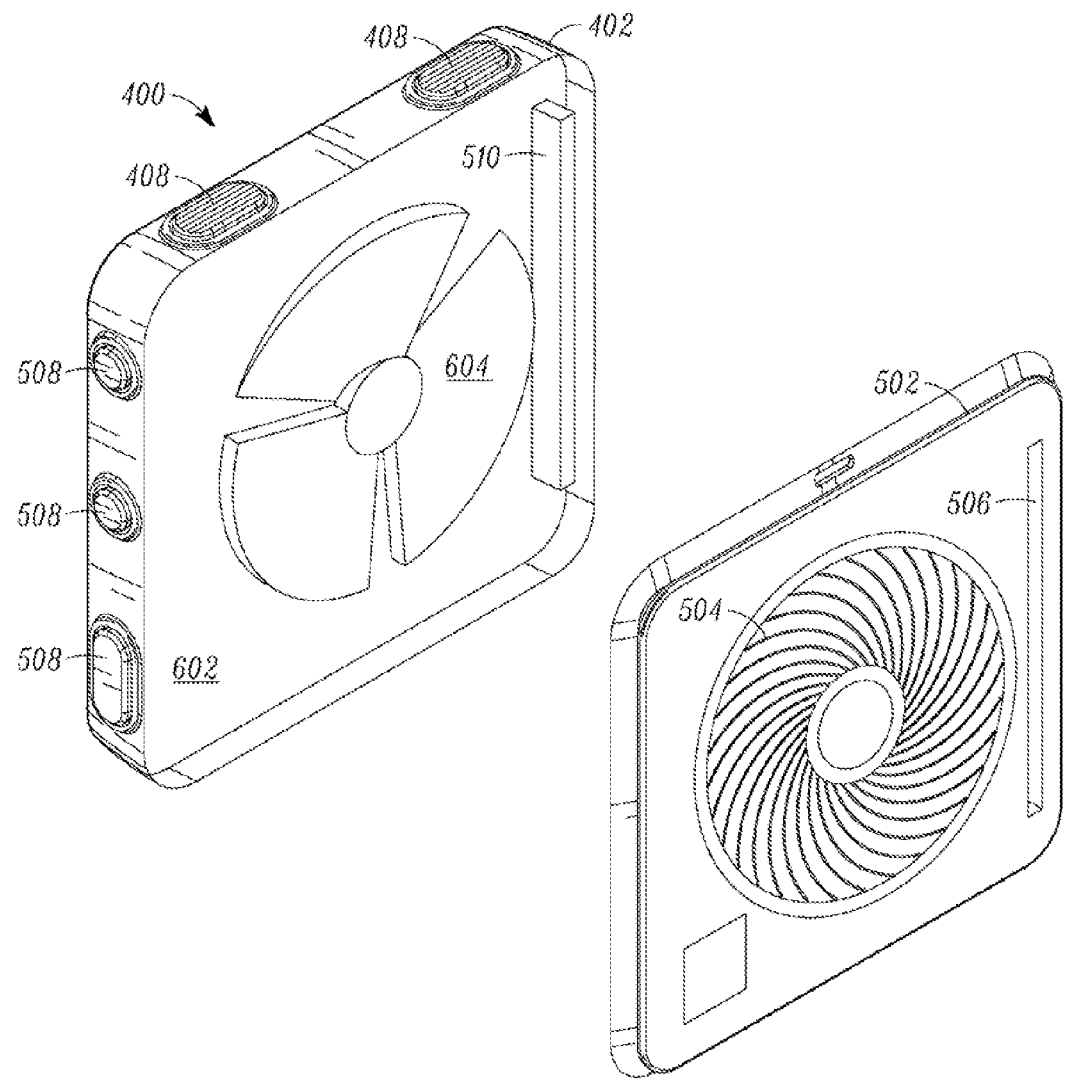
FIG. 6 illustrates an oblique view of the back side the of fragrance emission device of FIG. 4, wherein the back side is separated from the body.

FIG. 6 illustrates an oblique view of back side 502 of fragrance emission device 400, wherein back side 502 is separated from body 402. As shown in the figure, an inner portion 602 of fragrance emission device 400 includes a fan 604. Additionally shown in the figure, fragrant material 510 is disposed within inner portion 602, near fan 604.

A portion corresponding to each portion of fragrance emission device 102 of FIG. 1 is not shown in fragrance emission device 400. FIGS. 4-6 serve to illustrate a non-limiting example of the material distribution. With additional reference to FIG. 1, in fragrance emission device 400, display screen 404 corresponds to interface portion 110, whereas fan 604 may correspond to material dispenser 104.

In operation, a user may turn on fragrance emission device 400 via power button 406. Actuating buttons 508 may be used to enter information, override a fragrance mission, etc. When a fragrance is to be emitted, fan 604 may rotate, wherein air is sucked in through air intake vents 408. Air turbulence is created from the rotation of fan 604 within inner portion 602. The turbulent air swirls around fragrant material 510 creating fragrant air. The fragrant air is then expelled out through exhaust vent 504 and around the user of fragrance emission device 400.

Fragrance emission mechanism of device 400 as shown in FIGS. 4-6, is but a single-non limiting example. Any known fragrance (or odor-neutralizing, as discussed above) emitting mechanism may be used in accordance with example embodiments. Another material dispensing mechanism is shown in FIG. 7.

Figure 7:
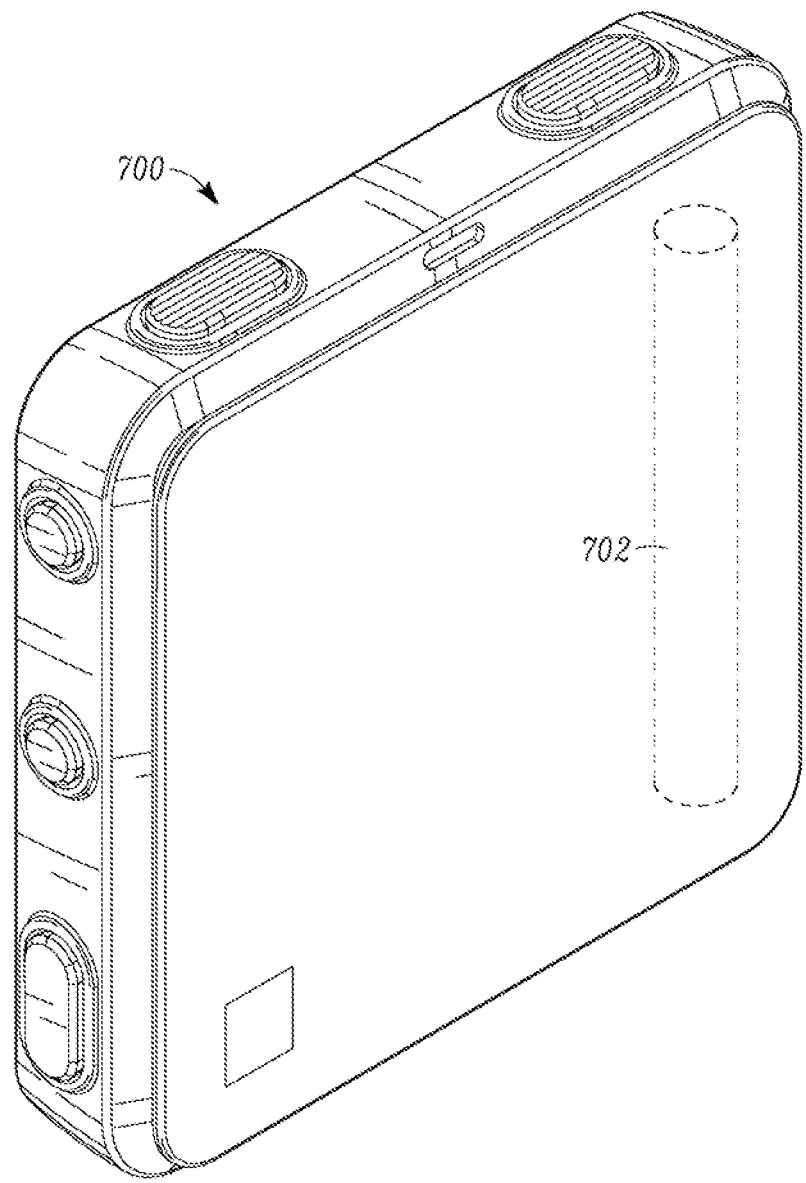
FIG. 7 illustrates an oblique view of a front side of another example fragrance emission device.

FIG. 7 illustrates an oblique view of a front side of another example fragrance emission device 700. As shown in the figure, fragrance emission device 700 is similar to fragrance emission device 400 of FIGS. 4-6. Fragrance emission device 700 differs from fragrance emission device 400 in that fragrance emission device 700 includes a canister 702 of a liquid fragrant material, as opposed to fragrant material 510. Canister 702 may be any known type of liquid fragrant material dispenser that is able to controllably release sufficient liquid to provide the fragrance within the turbulent air to be expelled through exhaust vent (not shown) and around the user of fragrance emission device 700. Canister 702 may be controlled by one or more processors for the fragrance emission device.

Conventional automatic fragrance emission devices emit fragrances in response to physical characteristics such as body temperature.

In contrast with conventional automatic fragrance emission devices, embodiments of the present invention predict when a fragrance may be needed. Further, embodiments of the present invention provide a user notification of an impending fragrance emission. Still further, embodiments of the present invention provide a user override to prevent an impending fragrance emission. Additionally, embodiments of the present invention provide alternate suggested routes of travel based on a predicted need of a fragrance.

The foregoing description of various preferred embodiments have been presented for purposes of illustration and description. It is not intended to be exhaustive or to limit the invention to the precise forms disclosed, and obviously many modifications and variations are possible in light of the above teaching. The example embodiments, as described above, were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A portable device comprising:
a sensor operable to detect a physical activity of a user;
an odor prediction portion in communication with the sensor and configured to generate an indication of predicted user odor based on detected physical activity of the user;
a communication portion operable to access one or more social networks via a communication network, wherein the device is capable of communicating with a social network of contacts; and
a route suggesting portion operable to provide a suggested route away from a set of defined persons within the social network of contacts responsive to the indication of the predicted user odor.

2. The device of claim 1, wherein the one or more social networks include a social structure that is connectable over a wireless or wired communication network.

3. The device of claim 2, wherein the social structure includes a set of actors and dyadic ties between these actors.

4. The device of claim 1, wherein the one or more social networks include at least one website that allows individuals to compile a list of friends, contacts or business associates and communicate with those contacts via the communication network.

5. The device of claim 1, further comprising a parameter detector configurable to select from a group consisting of an accelerometer, galvanic skin response monitor, a biometric sensor, an environmental sensor, a location-based sensor, context, and a camera.

6. The device of claim 1, further comprising a material dispenser operable to dispense a fragrant material at a future time based on a prediction signal.

7. The device of claim 6, wherein said material dispenser comprises one of a group consisting of a spraying device, a fan and a heating device.

8. The device of claim 6, wherein said material dispenser is conditionally operable to dispense the material based on at least one parameter selected from a group consisting of sweat history of a device user and medical history of the device user.

9. The device of claim 6, wherein said material dispenser is operable to conditionally dispense the fragrant material based on a location of another person relative to the device.

10. The device of claim 6, further comprising an alert module providing a notification of an impending dispensing of the fragrant material by said material dispenser.

11. The device of claim 10, further comprising an override portion operable to prevent said material dispenser from dispensing the fragrant material.

12. The device of claim 1, further comprising an odor sensor configured to detect a change in odor intensity.

13. A device of claim 1, further comprising:
a suppressor operable to output a suppression signal based on the odor prediction signal; and
a material dispenser operable to dispense a fragrant material based on the detection signal and the suppression signal.

14. A device of claim 1, wherein the route suggesting portion is operable to output a suggested route indicator based on an odor prediction signal and tracking of social contacts along a mutually traveled route.

15. The device of claim 14, wherein the suggested route indicator is additionally based on historical traffic patterns that the device has previously traveled.

16. The device of claim 14, wherein the suggested route indicator is additionally based on possible ventilation present on the suggested route.

17. A method comprising:
generating, via an activity sensor, a detection signal based on a physical activity of a user of a portable device;
generating an indication of predicted user odor based on the detection signal;
accessing, via a communication portion, one or more social networks via a communication network, wherein the device is capable of communicating with a social network of contacts; and
outputting, via a route suggesting portion, a suggested route away from a set of defined persons within the social network of contacts responsive to the indication of the predicted user odor.

18. The method of claim 17, wherein the one or more social networks include a social structure that is connectable over a wireless or wired communication network.

19. The method of claim 18, wherein the social structure includes a set of actors and dyadic ties between these actors.

20. The method of claim 17, wherein the one or more social networks include at least one website that allows individuals to compile a list of friends, contacts or business associates and communicate with those contacts via the communication network.

* * * * *